United States Patent [19]

Allen et al.

[11] 4,183,247

[45] Jan. 15, 1980

[54] METHOD FOR SAMPLING AIR IN PROPORTION TO RESPIRATION

[75] Inventors: Richard T. Allen, Easton, Md.; Rudolph H. Moyer, West Covina, Calif.; Donald J. Sibbett, Cucamonga, Calif.; Howard H. Anderson, Covina, Calif.; Glen R. Martner, Rosemead, Calif.; Don Willis, Garden Grove, Calif.

[73] Assignee: Geomet, Incorporated, Gaithersburg, Md.

[21] Appl. No.: 901,654

[22] Filed: May 1, 1978

[51] Int. Cl.² .............................................. G01N 1/22
[52] U.S. Cl. .................................. 73/421.5 R; 128/719
[58] Field of Search ......................... 73/421.5 R, 24; 128/2.08, 2 C, DIG. 29, 719

[56] References Cited

U.S. PATENT DOCUMENTS

| 2,194,809 | 3/1940 | Powell, Jr. | 128/2.08 |
| 2,284,147 | 5/1942 | Herrick | 73/421.5 R X |
| 3,097,639 | 7/1963 | Streimer | 128/2.08 |
| 3,316,902 | 5/1967 | Winchel et al. | 128/2.08 |
| 3,410,059 | 11/1968 | Garnier | 55/270 |
| 3,483,861 | 12/1969 | Tiep | 128/2.08 |
| 3,661,528 | 5/1972 | Falk | 128/2 C |
| 3,782,368 | 1/1974 | Reibold | 128/DIG. 29 |
| 3,802,250 | 4/1974 | Garnier | 73/28 |
| 3,956,940 | 5/1976 | Guild | 73/421.5 R |
| 4,080,832 | 3/1978 | Moody et al. | 73/421.5 R |

FOREIGN PATENT DOCUMENTS

1480160 4/1967 France .................................... 128/2.08

Primary Examiner—Daniel M. Yasich
Attorney, Agent, or Firm—David H. Semmes

[57] ABSTRACT

Method for sampling air in proportion to respiration, particularly the collection of air pollutants in proportion to the actual respiration of the wearer. The method is characterized by its use of a pump supported adjacent the thoracic cavity and activated by the expansion and contraction of the thoracic cavity during respiration, so as to draw air through an air sampling monitor.

1 Claim, 11 Drawing Figures

METHOD FOR SAMPLING AIR IN PROPORTION TO RESPIRATION

CROSS REFERENCES TO RELATED APPLICATIONS

Other copending applications are Ser. Nos. 901,653, 901,861 and 901,862, all filed on May 1, 1978.

BACKGROUND OF THE INVENTION (1) Field of the Invention

Although a considerable variety of instrumentation such as impingers, cascade impactors, battery powered air samplers, diffusion collectors and gas-stain detector tubes has been developed for application in monitoring ambient and industrial atmospheres, none may be considered to measure the exposure of an individual to noxious airborne components. All electrically powered and diffusion collection devices fail to measure the varied intake of undesirable gases and particulates which are inhaled into the lungs of an individual, as diverse demands for oxygen are met in response to a range of physiological activities. Thus, exposure to deleterious gases or particulates during periods of high levels of physical activity which result in deep and rapid inspiration are weighed equally in a statistical sense, with periods of shallow breathing in a clean environment by collection devices which sample air in uniform rates. For more accurate correlation with health phenomena it is highly desirable that air sampling for analytical determinations be proportional to the ventilation rate of the individuals under study.

2. Description of the Prior Art

Being submitted separately under the provisions of 37 C.F.R. 1.97.

SUMMARY OF THE INVENTION

Method for sampling air pollution in proportion to respiration, comprising supporting an air sampling monitor adjacent the mouth of a respirant human or animal, pumping air through the sampler, according as the thoracic cavity expands and contracts and gauging the amount of pollutants collected within the air sampling monitor as the amount of pollutants actually inhaled by the respirant during a given period. The method includes generating electric signals proportionate to the volume of air being pumped and displaying accumulated signals in digital readout, as a function of total volume of air being inhaled by the respirant. The total volume of air is correlated with the amount of pollutants collected within the air sampling monitor during the given period.

DESCRIPTION OF THE PREFERRED EMBODIMENTS

The invention consists of a method and apparatus for utilizing the expansion and contraction of the chest cavity to drive an air sampling system. The suggested apparatus comprises a self-powered pump, a method for measuring the volume of air, a device for indicating the air volume, a belt or envelope to be fastened around the lower chest or upper abdominal region which supplies mechanical power to drive the pump and a vest or harness to support the components. Weight and size minimization is a major requirement for all components.

The personally powered air sampler utilizes a diaphragm pump driven by a spring and belt in combination with an electronic signal accumulator and a separated digital readout. This method has the advantage of minimizing back-pressures which must be overcome by the respiratory action of the wearer. The sampling pump, a gas sampling assembly, an electronic signal accumulator and a digital readout. Each of these items is described below.

Vest

The vest 10 is made of a lightweight fabric such as nylon in order to minimize weight and motion resistance. It serves to support the belt 12, pump pocket 14, sampling assembly tube 16 and signal accumulator pocket 18. It may be manufactured with several size adjustments such as a Velcro closure and a conventional circumference adjustment in the rear. For universal usage, several sizes of vest may be required, however the functional components are constructed to fit any size wearer. Pump pocket 14 is connected through openings to belt 12 located either within or on the outside of vest 10. Pocket 18 is supplied for the miniature electronic signal accumulator and its battery. Loops 20 may be provided to keep belt 12 in position within or outside the vest material. The belt is partially sewed to the fabric of vest 10. Loops 20 and/or a fastenable flap are added to support the sampling tubes which are insertable within sampling pocket. Clips 22 may also be used to hold the vest in position with respect to the belt of the wearer and to fasten the sampling inlet at a desired location. Manifestly, a variety of vest or harness structures might be utilized satisfactorily.

Air Pump

Figure 1:
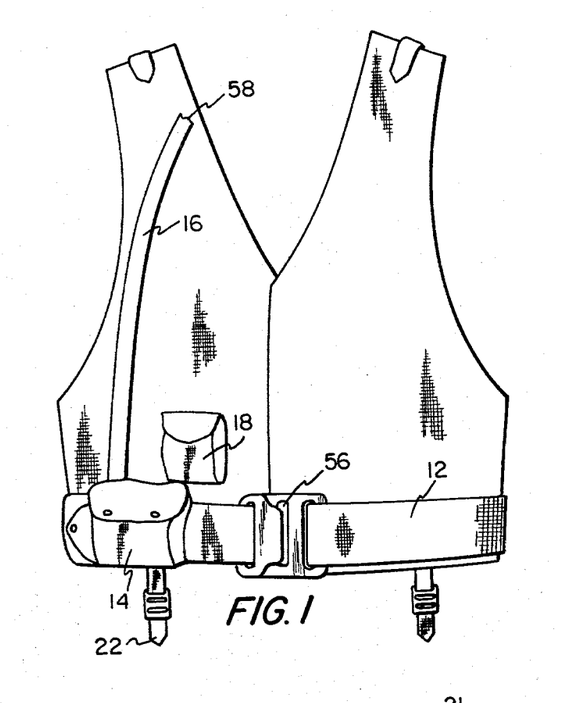
FIG. 1 is a front elevation of a personal monitor vest, secured by an adjustable belt, and supporting an air sampling tube, a pump mechanism and electronic signal and display circuit.
Figure 2:
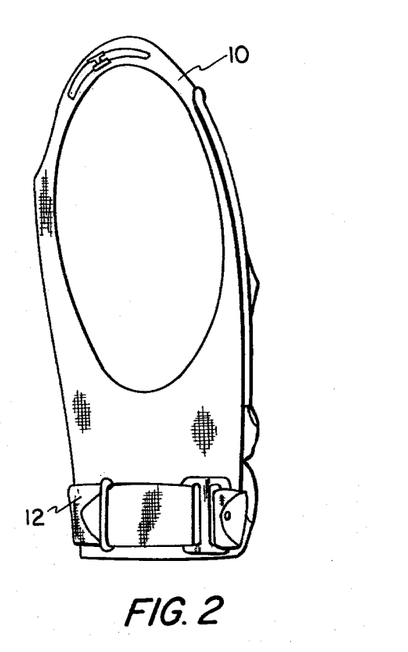
FIG. 2 is a side elevation from the right side.
Figure 3:
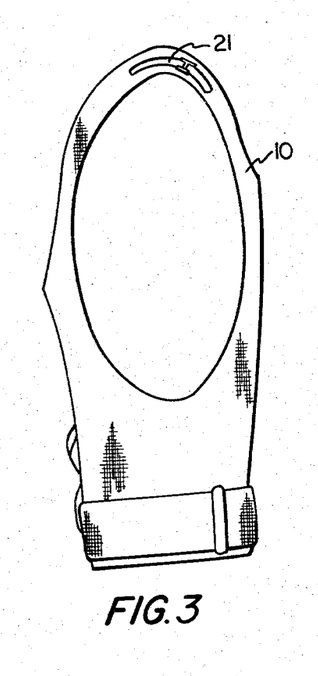
FIG. 3 is a side elevation from the left side.
Figure 4:
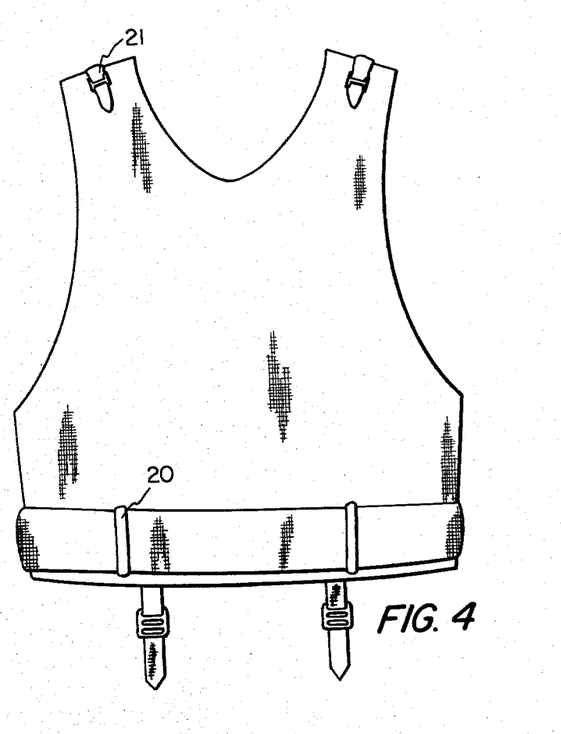
FIG. 4 is a rear elevation.
Figure 5:
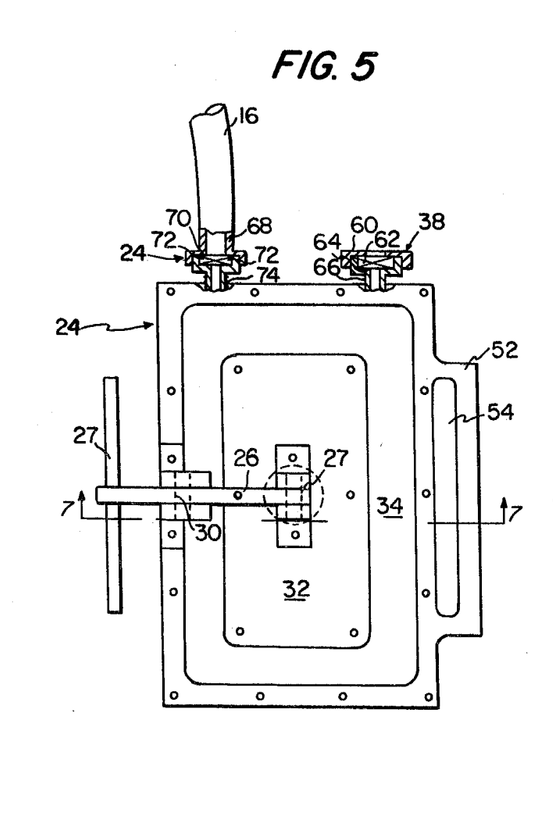
FIG. 5 is a fragmentary top plan partially in section of a proposed pumping unit.
Figure 6:
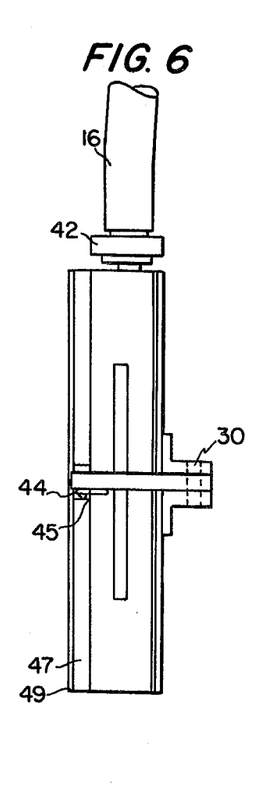
FIG. 6 is a side elevation.
Figure 7:
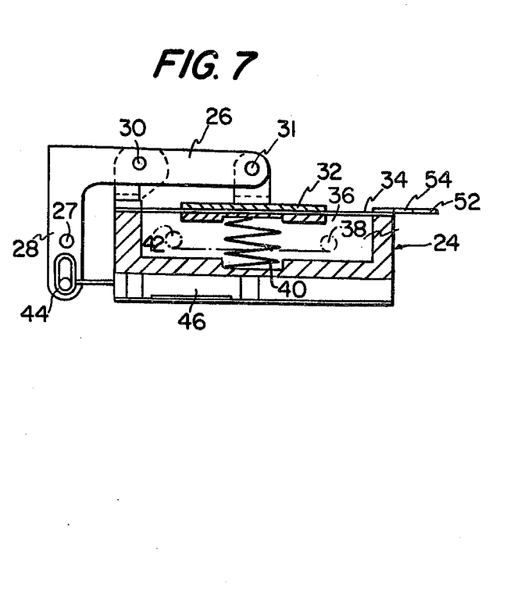
FIG. 7 is a vertical section, taken upon section line 7—7 of FIG. 5.

A mechanical configuration of an air pump 24 driven by torso expansion is shown in FIGS. 5–7. In principle it is a simple diaphragm pump. Operating through bellcrank 26, torso expansion as relayed by increased force on belt 12, pulls the bottom end 28 of bellcrank lever 26 outward pivoting the bellcrank arm around the crank pivot 30, such that crank link 31 forces the driver plate 32 downward against diaphragm 34. This process forces air out of the pump cavity 36 through the exhaust valve 38. Exhaust valve 38 may include body 66, enclosed by a perforated cap 60 and enclosing diaphragm 64 and spring 62. Upon relaxation of the pressure by the belt 12 on the bellcrank 26, a compression spring 40 under diaphragm 34 moves driver plate 32 by drawing air in through intake valve 42 and through the sampling tube assembly 15. This alternating movement of the diaphragm operating the conjunction with inlet valve 42 and exhaust valve 38 constitutes a small volume air pump. Intake valve 42 may include body 74, axially supporting compression spring 72 and diaphragm 70 with respect to tubular cap 68. The indication of pump driver movement is obtained by use of a linear potentiometer 46 which is connected by a switch link 44 to the lower arm 28 of the bellcrank beneath belt pin 27. As illustrated in FIG. 6, switch link 44 may include switch 45, riser 47 and cover 49. Movement of the contact of the linear potentiometer 46 in both directions is recorded by the accumulator circuit illustrated in FIGS. 8A and 8B. This signal gives the measure of the gas volume which passes through the pump and sampler. Manifestly, pump 24 may be constructed without exhaust valve 38, such that exhausted air is pumped outwardly through the sampling tube.

The pump 24 initially fabricated of aluminum with a latex or sheet plastic diaphragm 34 has no critical dimensions. It is readily fabricated in molded plastics for minimum weight. The diaphragm may be protected by another sheet of plastic film such as mylar.

Belt

The air sampling pump 24 is driven by the alternating tensions and relaxations applied by belt 12 operating in opposition to compression spring 40 within the pump. Belt 12 is fastened around the lower chest wall in a position so as to receive an optimum increase in pressure during inspiration. For convenience belt 12 is attached to vest 10 at several places by direct sewing as at 50 and bypassing loops 20. For example, one design attaches the belt 12 directly to vest 10 on both sides of the front closure. The vertical placement of belt 12 should be arranged, such that when the intercostal muscles contract and the ribs are pulled forward and upward increasing the diameter of the thoracic cavity a maximum tension is placed upon belt 12. Under these conditions, bellcrank arm 28 is pulled outward, away from pump 24 and, thereby, forces the pump driver plate 32 to push the pump diaphragm 30 inwardly. Pump 12 may include cover 52, having one or more belt loops 54.

Belt 12 is made of any non-stretching fabric such as webbing or tightly woven canvas. It is usually attached to vest 10 on the sides; the length between these attachments is adjusted by sliding the belt through loop 54 in the pump cover followed by fastening the loop end of the belt 12 with one of many types of fasteners 56 a small buckle or a Velcro section. The fastening must remain fixed during the period of use, the sampling interval.

Signal Accumulator

Figure 8A:
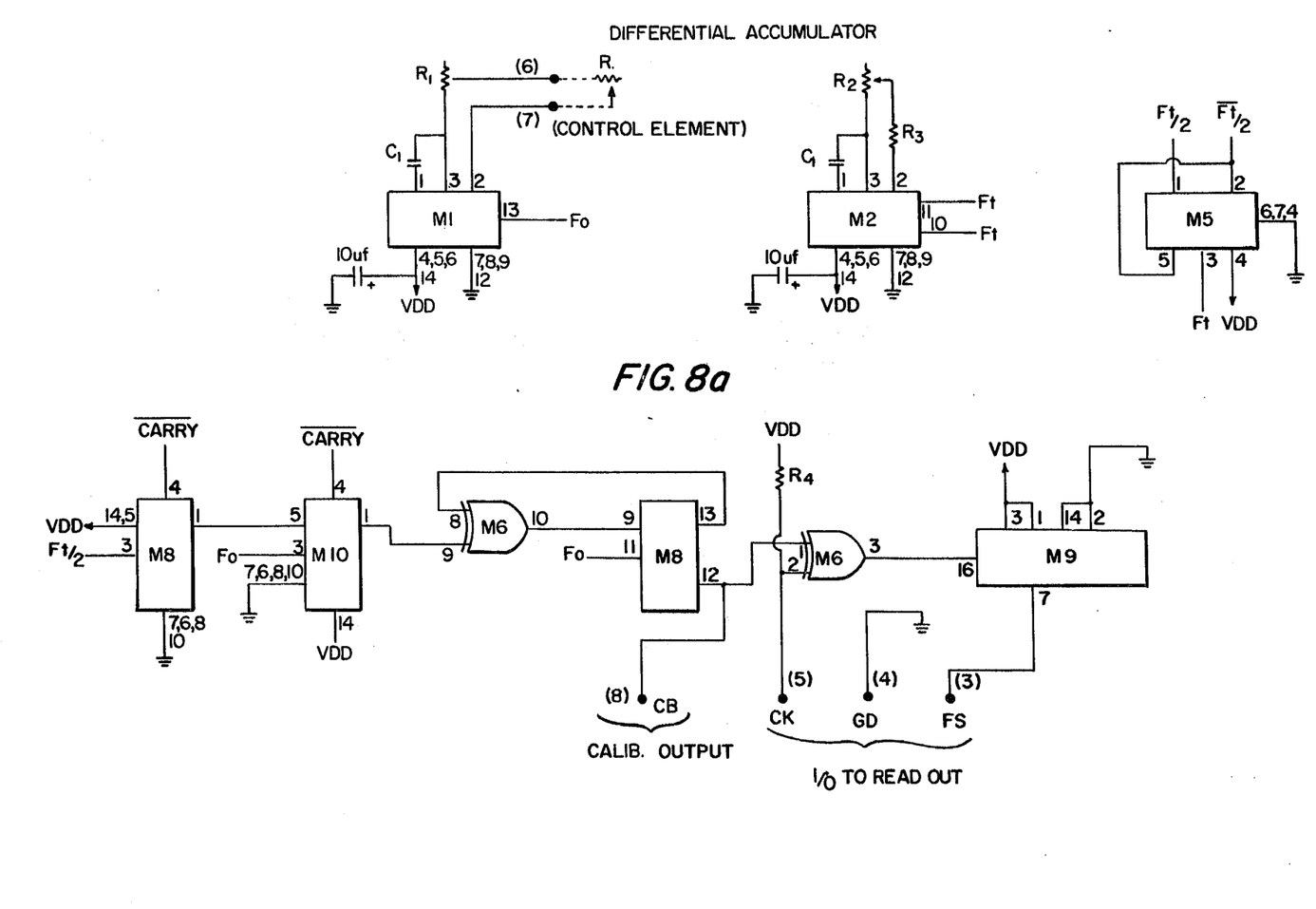
FIGS. 8A and 8B are circuit diagrams of a differential accumulator wherein electric signals proportionate to the volume of air being pumped and accumulated.
Figure 8B:
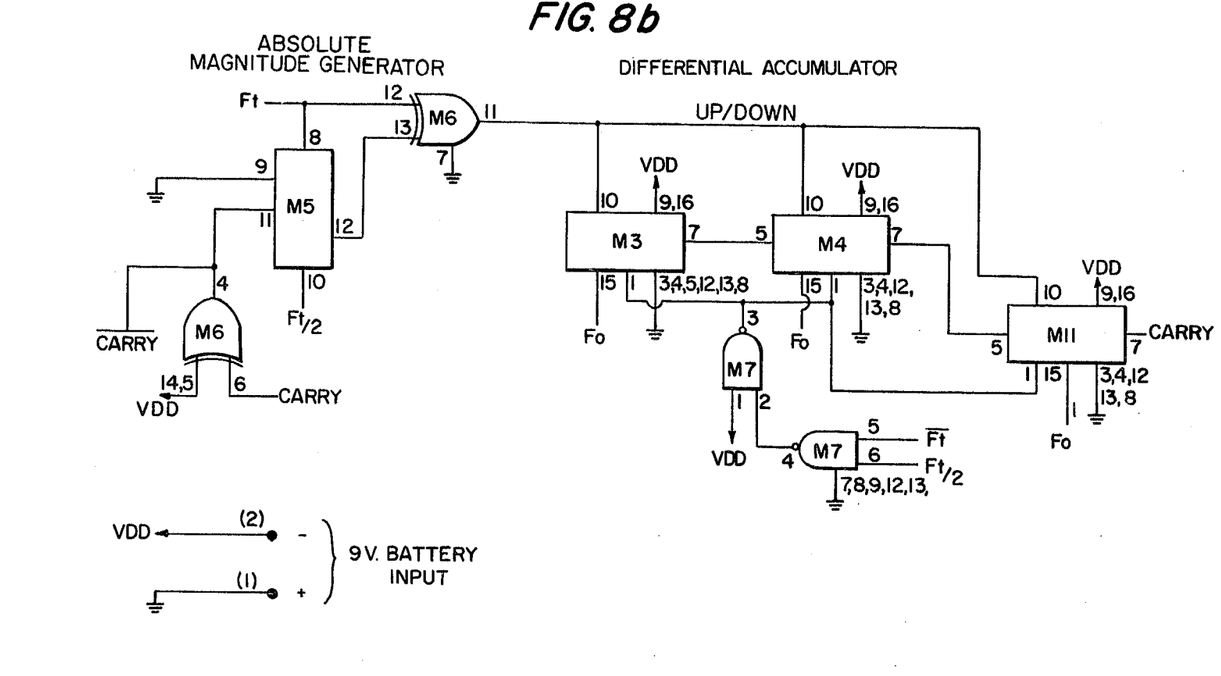
Figure 9A:
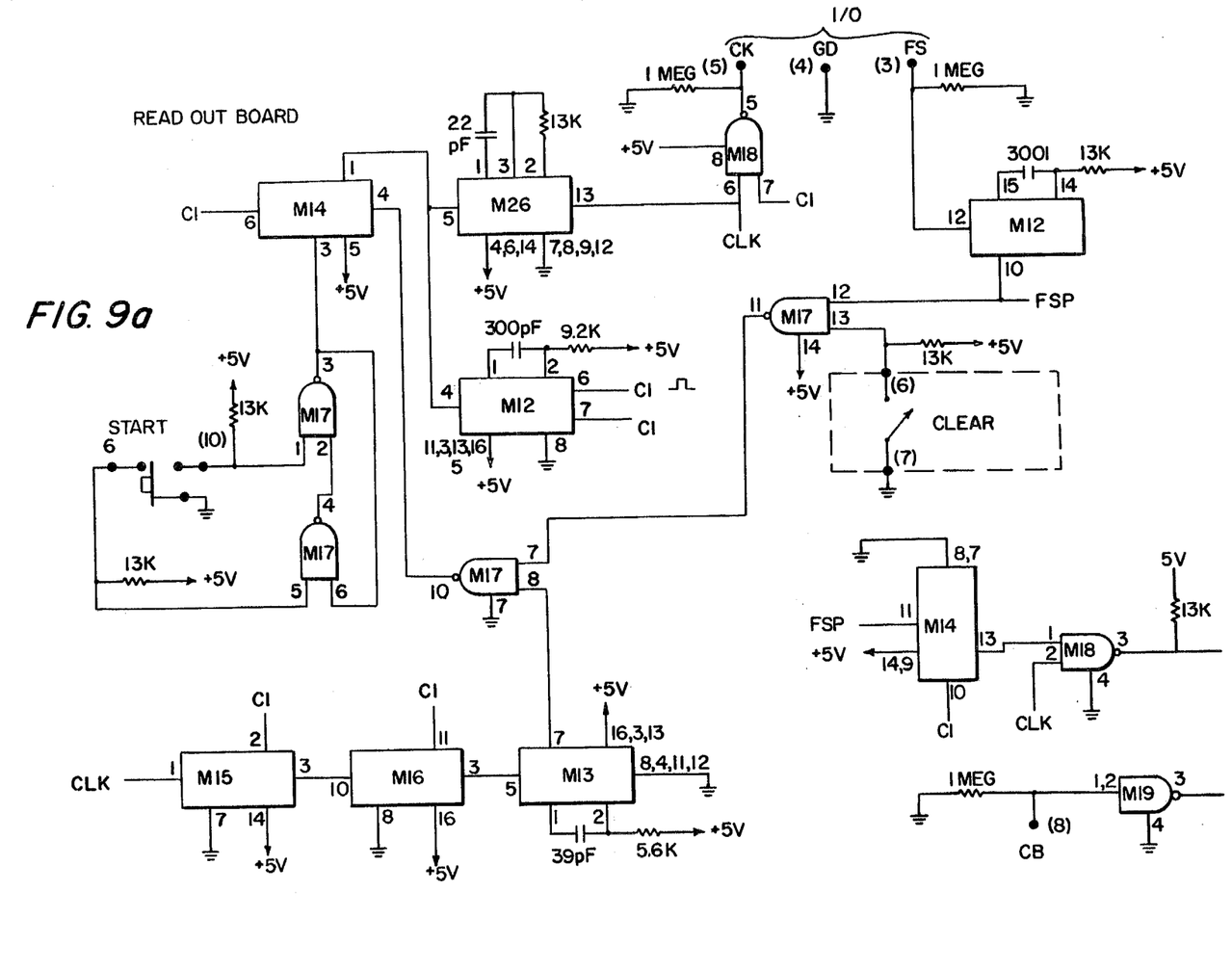
FIGS. 9A and 9B are circuit diagrams of a readout display where the accumulated signals are displayed digitally as the total volume of air displaced.
Figure 9B:
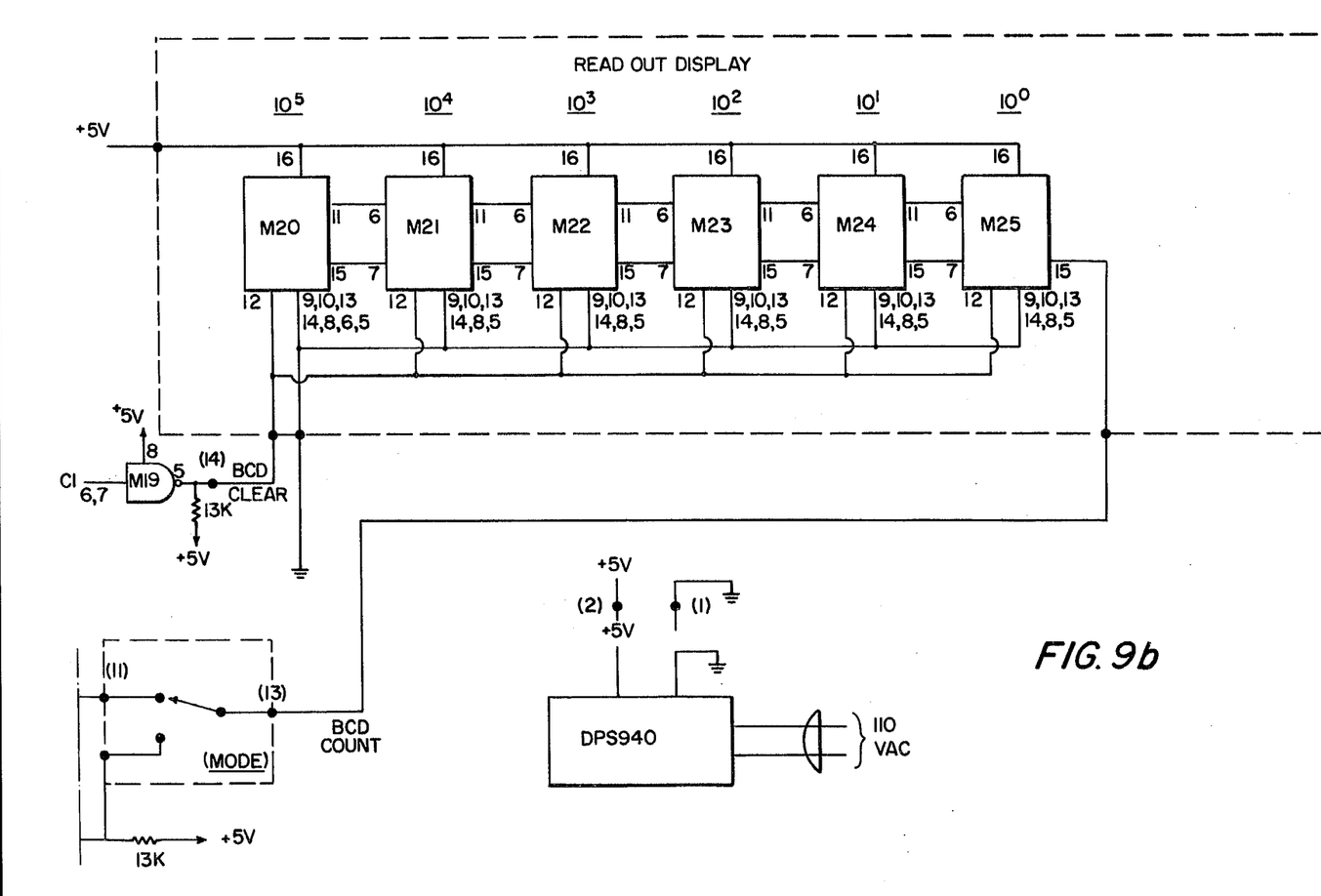

A proposed signal accumulator circuit is illustrated in FIGS. 8A and 8B. The signal accumulator is a device which indicates total volume of air displaced by an individual's breathing during a given period of time. The accumulator operates in conjunction with the pump module, in which a resistive (or capacitive) sensing element is an integral member. Variation of resistance (or capacity) of the sensing element is in proportion to the air volume pumped and also displaced by the individual's lungs. Total resistive (or capacitive) variation is sensed and processed by the accumulator, which in turn, generates a count electronically proportional to total air volume displacement. The accumulated count is virtually independent of the rate of air volume displacement. When connected, such as is illustrated in FIGS. 9A and 9B, to a readout unit, the accumulated count is displayed in decimal format indicating total air volume displacement.

Accumulator Circuit Diagram

As indicated in the circuit diagram in FIGS. 8A and 8B, the accumulator consists of the following elements; sensor to frequency converter, up-down counter and count accumulator. The sensor to frequency converter translates the specific sensor resistance (or capacitance) to a proportional frequency of output pulses. The up-down counter increments with each converter output pulse for a given period of time, then decrements with each converter output pulse for an equal period of time. Following the up-down count, the absolute value of the count remaining in the up-down counter is transferred to the count accumulator. The up-down counter is then cleared to zero and the process repeats.

If the resistance or capacity of the sensing element remains constant during the up-down counting periods, the frequency of the converter will also remain constant. It is evident in this situation that the number of incrementing pulses during the up counting period is equal to the number of decrementing pulses during the down counting period (both periods always equal). The resultant count (zero) is transferred to the count accumulator. Therefore, a constant sensor magnitude, indicating no air displacement, will provide zero input count to the accumulator for an indefinate period of time.

If, however, the sensor element is changing (let us initially assume to cause a decreasing converter output frequency) the product of the average frequency change (Delta S) during the counting interval, times the counting interval (T) will be the residual count transferred to the count accumulator. This is evident, since with continually decreasing frequency more incrementing counts occur during the up count period than decrementing counts during the down count period (of diminished frequency) which follows. Likewise, an equivalent sensor change in the opposite direction will generate an increasing converter frequency. This average frequency change (minus Delta S) times the counting interval (T) will provide a negative residual count of equal magnitude to the decreasing frequency case above. However, since the absolute value of the residual count is transferred to the count accumulator, an increase in the accumulator count of equal magnitude to the decreasing converter frequency case above will be realized. Thus any sensor variation (increasing or decreasing, which in turn is a function of air displacement) will provide a proportional increase in accumulator count.

Minimizing the following parameters was of paramount consideration in the accumulator design:
1. COST
2. VOLUME (TOTAL NUMBER OF COMPONENTS)
3. POWER CONSUMPTION
4. READOUT CONTRACTS Cost minimization is accomplished by utilizing CMOS integrated circuits of most common usage (minimum initial procurement cost). The design implementation requires only nine integrated circuits for all accumulator functions. Printed circuit board area of the accumulator will be approximately 2¼" square. In addition, all integrated circuits of the accumulator are available in chip form. Thus, a single hybrid circuit consisting of the nine IC chips deposited on a ceramic substrate and contained within a single package ½"×1"×⅛" is economically attractive for production quantities. Utilizing complementing MOS integrated circuits provides the absolute minimum power requirement attainable. With the exception of the sensor to frequency converter, all remaining functions require only microwatts of power. A miniature inexpensive 9 volt transistor radio battery will provide accumulator power for approximately 10 weeks. Only three contacts are required for connection of the readout unit. A standard miniature phone jack may therefore be used for quick connect/disconnect of the readout unit. A dust cover provides environmental protection of the accumulator readout receptacle.

Since resetting the accumulator requires connection of a readout unit, the wearer, short of refusal to breathe, is unable to alter the accumulator data.

At procurement, a certain variance of characteristics of the sensor to frequency integrated circuits will exist. However, two trimpot adjustments in the accumulator circuit will normalize the variations such that all pneumatic belts (and accumulators) may be identically calibrated.

METHOD FOR SAMPLING AIR IN PROPORTION TO RESPIRATION: CIRCUITRY DESCRIPTION

Admitted Known elements of "Accumulator", FIGS. 8a and 8b:

M1, M2=CD4047A (Multivibrator)
M3, M4, M11=CD4029A (Up-Down Counter)
M5, M8, M10=CD4013A (Dual "D" Flip Flop)
M6=CD4030A (Quad Exclusive or Gate)
M7=CD4011A (Quad 2 Input Nand Gate)
M9=CD4045A (21 Stage Counter)

Admitted Known Elements of "Read Out Device", FIGS. 9a and 9b:

M12, M13=CD4098B (Dual Monostable Multivibrator)
M14=CD4013A (Dual "D" Flip Flop)
M15=CD4024A (7 Stage Counter)
M16=CD4020A (14 Stage Counter)
M17=CD4011A (Quad Tow Input Nand Gate)
M18, M19=CD40107B (Dual 2 Input Nand Buffer)

Referring to FIG. 8a, the basic clock frequency is generated by a stable multivibrator M1. This frequency is a function of the resistance of the external control element (R). The control element is attached to the sensor diaphragm and its resistance is therefore a function of diaphragm position. As the sensor diaphragm is displaced, either inward or outward, the clock frequency (M1-13) varies accordingly. If the position of the sensor diaphragm is stationary, the clock frequency, in turn, remains constant.

A stable multivibrator M2, in conjunction with the adjacent flip flop M5, provides a fixed time base. Multivibrator output Ft is a square wave complement of $\overline{Ft}$. This is a fixed and significantly lower frequency than the sensor clock Fo. Flip flop M5 divides Ft by two generating complementary square wave outputs Ft/2 (M5-1) and $\overline{Ft/2}$ (M5-2) at one half the Ft frequency.

Referring to FIG. 8b; M3, M4 and M11 form a 12 stage binary up-down counter. Flip flop and gates M5, M6 and M7 form up-down control logic. Together they provide a differential accumulator, which extracts the difference in Fo clock pulses of two adjacent Ft half cycle periods. Description of the differential accumulator operation may be aided by the following diagram:

FIGURE A

Periods A, B, C and D are of equal duration. During the entire A period, M6-12 (Ft) is at a high level and M6-13 is low. This causes the up-down control line, which is the exclusive or output M6-11, to remain high. In the high state the up-down control line causes the M3, M4, M11 up-down counter to increment with each Fo clock pulse. During the following period (B), Ft steps low setting the exclusive or output (up-down control line) low. With the up-down control line low, the up-down counter decrements upon each Fo clock pulse. The up-down control line remains low during B unless a carry pulse is generated. If a carry pulse is generated during period B, the control flip flop M5 will toggle setting the up-down control line high. All Fo clock pulses subsequent to the carry pulse would therefore cause the counter to increment.

The following three possibilities exist during periods A and B:

1. The average clock frequency (Fo) during period A is equal to the average frequency during period B. This represents a situation of no diaphragm movement (no respiration).
2. The average clock frequency during period A exceeds the average clock frequency during period B. This represents a situation in which the diaphragm is moving in an expanding direction (expanding respiration).
3. The average clock frequency during period A is less than the average clock frequency during period B. This represents a situation in which the diaphragm is moving in a contracting direction (contracting respiration).

In the first situation the up-down counter will increment $F_A \cdot T_A$ times during period A. $F_A$ is the average clock frequency during period A and $T_A$ the period duration. Subsequently, the counter will decrement $F_B \cdot T_B$ times during period B. $F_B$ equals the average clock frequency during period B and $T_B$ the period duration. The remaining count ($C_R$) in the up-down counter at the end of period B is $C_R = F_A T_A - F_B T_B$. Since the average clock frequency of Period A is equal to that of period B and the periods are also equal, $F_A \cdot T_A + F_B T_B$ and $C_R=0$. This count (zero) is then added to a large capacity general accumulator M9. The general accumulator stores a count which is proportional to total respiration over a long interval (hours or days).

During period A of the second situation, an incremental count of $F_A \cdot T_A$ is generated in the up-down counter. Decremented from this count during period B is $F_B \cdot T_B$. Since $T_A$ equals $T_B$ and $F_A$ exceeds $F_B$ (expanding respiration), the resultant count in the up-down counter at the end of period B is, $C_R = F_A T_A - F_B T_B$. Again this count $T(F_A - F_B)$, which is proportional to expanding respiration, is added to the general accumulator.

The third situation increments the up-down counter $F_A \cdot T_A$ during period A. During period B the up-down counter decrements at the rate of $F_B$. However, since $F_B$ exceeds $F_A$ the up-down counter will decrement the entire $F_A \cdot T_A$ count of period A prior to the end of period B. At this point (prior to the end of B) the count of the up-down counter will equal zero and a carry pulse will be generated at M11-7. The carry pulse will appear inverted at M6-4, toggling flip flop M5. This changes the state of the up-down control line (M6-11) from low to high, such that all subsequent Fo pulses during period B will cause the counter to increment. The result is a positive count of quantity $F_A T_A - F_B T_B$, which is also the absolute value of the count differential between periods A and B ($C_R = |F_A \cdot T_A - F_B \cdot T_B|$). The count generated in the up-down counter at the end of period B is therefore a positive value of magnitude proportional to either expanding or contracting respiration.

During period C the count of the up-down counter (differential accumulator) is added to the contents of the general accumulator, M9. Since Ft and Ft/2 are both high, M6-11 and M6-13 are also high. This provides a low level on the up-down control line (M6-11), causing the up-down counter to decrement. As the up-down counter decrements towards zero the 21 stage general accumulator (M9) increments. The general accumulator is enabled to increment by a high level at M6-9. With M6-9 high, each Fo pulse at M8-11 causes the M8 flip flop to toggle. This square wave (M8-12) passes through M6-1 and M6-3 to the accumulator input M9-16. A scaling factor of two therefore exists between the decrement rate of the up-down counter and the increment rate of the general accumulator. The count which is added to the accumulator after periods A and B is, however, proportional to respiration during A and B. The high level at M6-9 (which allows M8 to toggle) is generated by the rising edge of Ft/2 (M8-3) at the beginning of period C. This rising edge sets the output M8-1 high. After the first Fo pulse at M10-3, the M10 output (M10-1) rises also. While M10-1 and M6-9 remain high, flip flop output M8-12 toggles with each Fo pulse and the general accumulator increments on every other toggle. This condition exists until the up-down counter decrements to zero and a carry pulse is generated. Upon the carry pulse, flip flop outputs M8-1 and M10-1 are cleared to a low level and incrementing of M9 terminates.

During period D, a high level on the up-down counter preset line (M3-1, M4-1 and M11-1) holds the counter to a zero count level. The preset condition is established by high levels of $\overline{Ft}$ (M7-5) and Ft/2 (M7-6). This generates a low level at nand gate output M7-4 and a high level at M7-3 (preset line).

The long term count accumulated by the general accumulator M9 is read out by an external device. When the external read out device is connected to the accumulator, clock pulses are applied to the CK input (M6-2). These pulses increment the accumulator (M9-16) until a (FS) full scale output results at M9-7. The number (N) of CK pulses required to advance the accumulator to full scale is subtracted from maximum counter capacity ($2^{21}$). The result ($2^{21} - N$) which is proportional to total respiration is displayed by means of LED decimal indicators on the front panel of the read out device. At the operator's option, the read out device may either leave the M9 accumulator at this state (cleared to zero for a new run, or return it to the original count (advance it $2^{21} - N$ counts) for continued operation of the same run.

Readout Subsystem

When a readout unit is connected to the accumulator, the content of the accumulator is displayed in decimal format. This display indicates total sensor variation, which is proportional to total air volume displacement by the individual's breathing. By using a select switch on the readout unit, the accumulator may be reset to zero, initiating a new interrogation period or the accumulator contents may be restored extending the existing interrogation period.

It is anticipated that calibration variations will exist between various individuals such that the proportionality factor, relating the inspiration volume with the pump sampling rate will vary. In usage for a measure of the time-average concentration of selected air pollutants determination of this proportionality is unimportant. However, where more exact dosage measurements are desired the system may be calibrated for each individual with a spirometer prior to extended use.

This efficiency coefficient for an individual may be entered by means of thumbwheel switches or a similar device into the readout unit prior to reading the air volume displacement. The display now directly indicates air volume displacement, for that particular individual, in liters. Determination of an individual's efficiency coefficient is easily accomplished and may be checked at infrequent intervals. The additional circuitry to incorporate an efficiency coefficient input into the readout device is minimal and conventional. It is not shown in the electronic schematic.

Sampling Subsystem

The sample air is drawn by pump 24 through dry or wet sample traps, depending upon the pollutant and technique selected for measurement and supported in sampling tube 16. The system described is generally useful for most pollutants. Determined by the chemical and physical properties of the selected pollutant the trap or traps may consist of a short section of coated tube, an absorbent bed either alone or in combination with an indicator, a small filter for particles, a miniature bubbler, an active gauze or an impregnated absorbent or reactant on a support. The sampler collector may be enclosed in any material which is appropriately chemically inert with respect to the pollutant. It is connected by inert tubing 16 between an inlet port 48 usually fastened in the vicinity of the neck, collar or shoulder of the individual and inlet valve 42 to pump 24.

For example, sulfur dioxide may be collected on a diffusion type collector which consists of a small bore plastic tube with an inner surface coated with potassium bicarbonate. A polypropylene tube (i.d. 3-5 mm) 15 cm in length with a roughened inner surface to retain the bicarbonate coating is used. It is connected at the upper end of the inlet tubing train. Its lower end is connected to the pump inlet valve 42 with a short section of tygon tubing. The diaphragm pump 24 produces an air intake rate of 75-120 ml per min. which passes through the coated section where, by diffusion, sulfur dioxide is transmitted to the adsorbent coated walls. On completion of the sampling interval, the coating is dissolved and analyzed by the pararosaniline or barium perchlorate method.

Similarly, vapors such as mercury may be sampled by placing a short section of silver gauze or wool within the sampler tube 16. Upon completion of sampling, the mercury is desorbed directly into an ultraviolet photometer by heating the silver wool or gauze in an induction furnace.

Likewise, organic vapors may be adsorbed on a small bed of a high surface area adsorbent such as Chromosorb 102, recovered after collection and analyzed.

Nitrogen dioxide may be collected on a diffusion tube coated with electrolytic lead dioxide.

Particulates mists and smokes may be sampled by use of a small microporous filter interposed in place of the gaseous collector.

Thus, a fall spectrum of pollutants may be collected by use of simple adsorbents or filters which are placed in the inlet line 16, ahead of the pump. The actual exposure of a wearer of the sampling system to one or a selection of pollutants may be determined on the basis of chemical or physical analysis of collected pollutants at the end of the sampling interval. The volume of air corresponding to the inhaled volume is determined from the accumulator and readout.

We claim:

1. Method for sampling air in proportion to respiration comprising:
    A. Supporting an air sampling monitor upon a respirant creature such that the open end of said monitor is adjacent the creature's mouth;
    B. Pumping air through said sampler by expansion and contraction of the thoracic cavity during respiration, said pumping including drawing air through said air sampling monitor, as said thoracic cavity contracts during exhalation and exhausting air, as said thoracic cavity expands upon inhalation;
    C. Gauging the amount of pollutants collected within said air sampling monitor, as a function of pollutant inhaled during a given period;
    D. Generating electric signals proportionate to the volume of air being pumped during each respiration;
    E. Accumulating said signals as a function of total volume of air being inhaled during a given period and displaying said accumulative signals in a digital readout of total air volume inhaled; and
    F. Correlating said digital readout of total air volume inhaled with the amount of pollutants collected in said air sampler, as a function of total pollutants inhaled.

* * * * *